US00PP24410P3

(12) United States Plant Patent
Dirr

(10) Patent No.: US PP24,410 P3
(45) Date of Patent: Apr. 29, 2014

(54) ***DISTYLIUM* PLANT NAMED 'PIIDIST-I'**

(50) Latin Name: ***Distylium* sp. hybrid**
Varietal Denomination: PIIDIST-I

(75) Inventor: Michael A. Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 416 days.

(21) Appl. No.: 13/068,262

(22) Filed: May 6, 2011

(65) Prior Publication Data

US 2012/0284885 P1 Nov. 8, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

PP23,128 P2 10/2012 Dirr
2012/0284884 P1 11/2012 Dirr

OTHER PUBLICATIONS

Plant Introductions, Inc.—promotional page from Plant Introductions website showing color pictures of *Distylium* Hybrids (*Distylium* hybrid 15 is *Distylium* plant named PIIDIST-I) downloaded May 5, 2011.

*Primary Examiner* — June Hwu
*Assistant Examiner* — Louanne Krawczewicz Myers
(74) *Attorney, Agent, or Firm* — Lathrop & Gage LLP

(57) ABSTRACT

A new and distinct cultivar of *Distylium* plant named 'PIIDIST-I', characterized by its compact, upright-spreading growth habit, yellow-green new growth, dark green mature foliage, and reddish purple flowers.

3 Drawing Sheets

Genus and species of plant claimed: *Distylium* sp. hybrid. Variety denomination: 'PIIDIST-I'.

BACKGROUND OF THE INVENTION

The present invention relates to a new and distinct cultivar of *Distylium* plant, botanically known as *Distylium* sp. hybrid, a member of the Hamamelidaceae, and hereinafter referred to by the cultivar name 'PIIDIST-I'.

'PIIDIST-I' originated as an open-pollinated seedling from seed collected from a *Distylium* sp. hybrid (*Distylium myricoides*×*D. racemosum*) growing in Watkinsville, Ga. 'PIIDIST-I' was selected in the summer of 2006 by the inventor in a cultivated environment in Dearing, Ga.

Asexual reproduction of 'PIIDIST-I' by stem cuttings, performed in Watkinsville, Ga., since 2006 has shown that all the unique features of 'PIIDIST-I', as herein described, are stable and reproduced true-to-type through successive generations of such asexual propagation.

SUMMARY OF THE INVENTION

Plants of the new cultivar 'PIIDIST-I' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIDIST-I'. These characteristics in combination distinguish 'PIIDIST-I' as a new and distinct cultivar: 1. Compact, upright-spreading growth habit; 2. Yellow-green new growth; 3. Dark green mature foliage; and 4. Reddish purple flowers.

Plants of 'PIIDIST-I' differ from plants of the parent, *Distylium* sp. hybrid, primarily in growth habit, foliage color, and cold hardiness, as plants of 'PIIDIST-I' have a smaller, more compact, upright-spreading growth habit, large lustrous dark green mature foliage, and increased cold hardiness, whereas plants of the parent have a larger, less compact, upright, spreading growth habit, smaller medium green foliage, and are less cold hardy.

Plants of the new *Distylium* 'PIIDIST-I' can be compared to plants of the cultivar 'PIIDIST-II' (U.S. Plant patent application Ser. No. 13/068,251), which is a sibling that originated from the same open-pollination. 'PIIDIST-I' has a compact, upright-spreading growth habit, yellow-green new growth, dark green mature foliage, and reddish purple flowers, whereas 'PIIDIST-II' has a compact, spreading growth habit, maroon-purple new growth, dark blue-green mature foliage, and reddish maroon flowers.

Plants of the new *Distylium* 'PIIDIST-I' can be compared to plants of the cultivar 'Vintage Jade' (U.S. Plant Pat. No. 23,128), which is a sibling that originated from the same open-pollination. 'PIIDIST-I' has a compact, upright-spreading growth habit, yellow-green new growth, dark green mature foliage, and reddish purple flowers, whereas 'Vintage Jade' has a compact, layered mounding and spreading growth habit, light green new growth, dark green mature foliage, and reddish maroon flowers.

BRIEF DESCRIPTION OF THE DRAWINGS

The accompanying color photographs illustrate the flower and foliage characteristics and the overall appearance of 'PII- DIST-I', showing the colors as true as it is reasonably possible to obtain in color reproductions of this type. Colors in the photographs may differ slightly from the color values cited in the detailed botanical description which accurately describe the colors of 'PIIDIST-I'.

DETAILED DESCRIPTION

Figure 1:
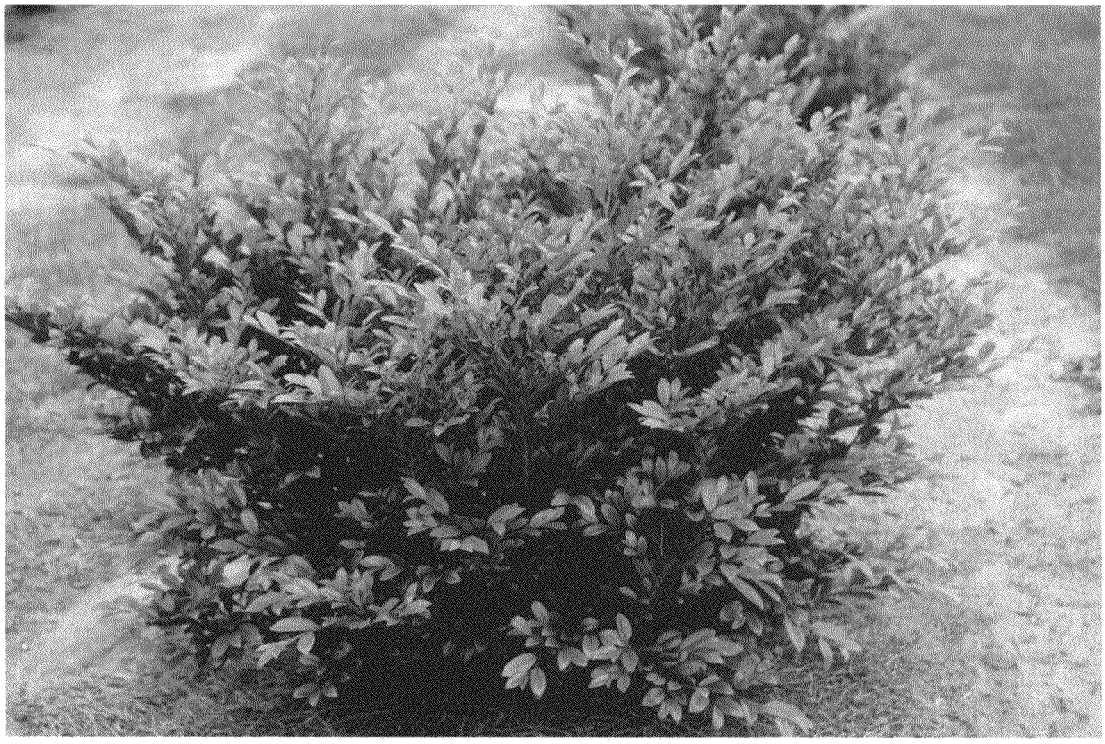
FIG. 1 illustrates the overall appearance and growth habit of 'PIIDIST-I'.
Figure 2:
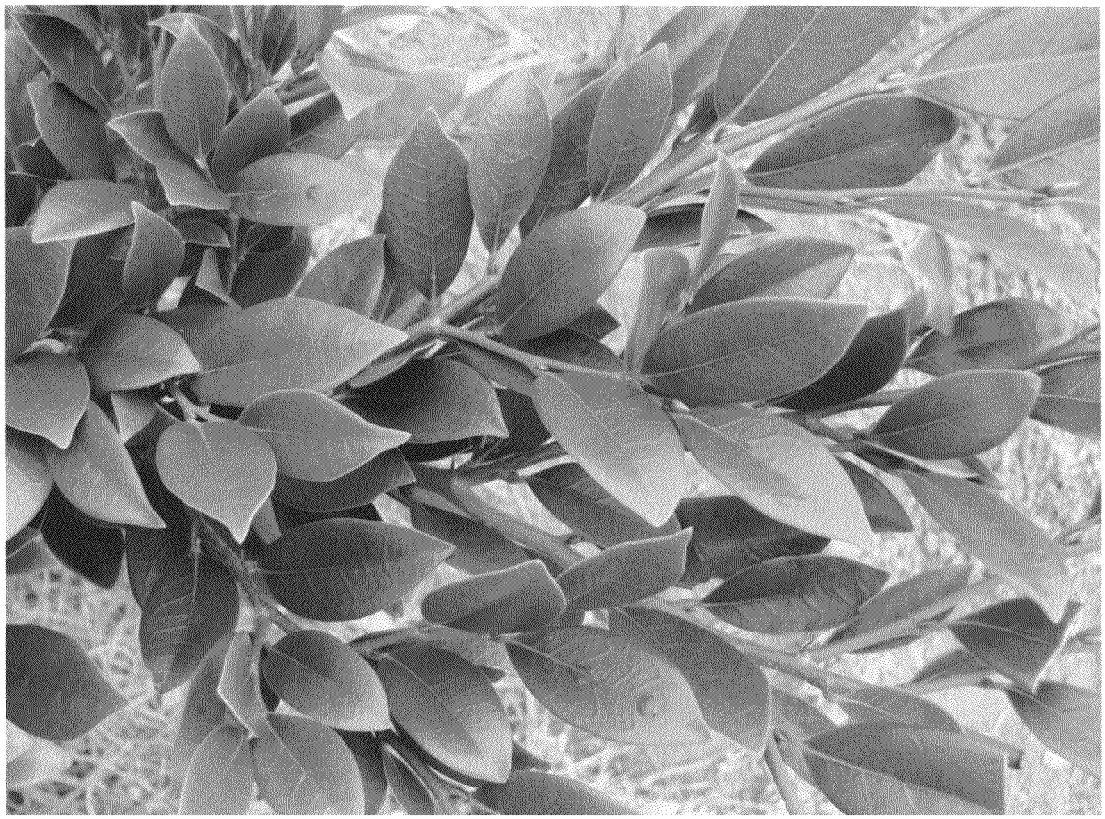
FIG. 2 illustrates a close-up view of the mature foliage of 'PIIDIST-I'.
Figure 3:
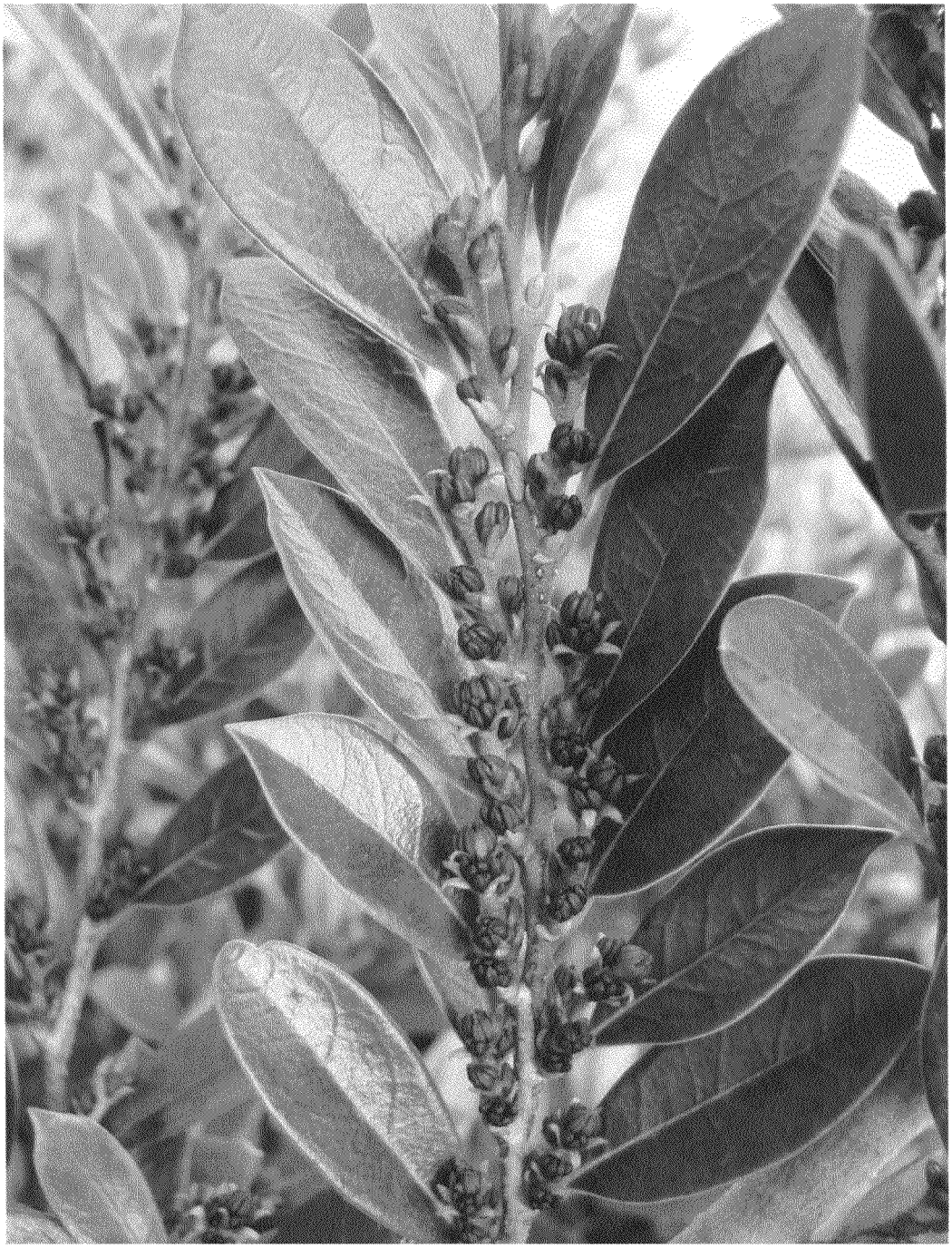
FIG. 3 illustrates a close-up view of the flowers of 'PIIDIST-I'.

In the following description, color references are made to The Royal Horticultural Society Colour Chart, 2001 Edition, except where general terms of ordinary dictionary significance are used. Plants used for the description were approximately 3-years-old and were grown in 11.8 L containers under outdoor conditions in Watkinsville, Ga.

Botanical classification: *Distylium* sp. hybrid, cultivar 'PIIDIST-I'.

Parentage: *Distylium* sp. hybrid.

Propagation: Stem cuttings.

Time to initiate roots in summer: About 3 to 4 weeks at 32° C.

Plant description: Broadleaf evergreen flowering shrub; multi-stemmed; compact, upright-spreading growth habit. Freely branching; removal of the terminal bud enhances lateral branch development.

- *Root description.*—Medium, well-branched.
- *Plant size.*—The original plant, now about five-years-old in the ground, is about 213 cm high from the soil level to the top of the foliage and about 274 cm wide.
- *First year stems.*—Having a diameter of about 2.5 mm. Shape: round. Fine pubescence. Few small lenticels about 1 mm in diameter and N199B in color.
- *First year stem color.*—146B.
- *Second year and older stems.*—Have a diameter of about 5 mm or more. Shape: round.
- *Second year and older stem color.*—199A.
- *Stem strength.*—Flexible when young, less flexible once mature.
- *Internode length.*—About 2 cm.
- *Trunk diameter.*—About 2.2 cm at the soil line.
- *Color.*—199A.
- *Bark.*—Does not exfoliate, covered with many lenticels about 2 mm in diameter and N199B in color.

Vegetative bud description:

- *Arrangement.*—Alternate.
- *Shape.*—Ovoid with fused, pubescent bud scales.
- *Size.*—About 3 mm in length and about 2 mm in width.
- *Color.*—N199A.

Foliage description:

- *Arrangement.*—Alternate, simple.
- *Length.*—About 4 cm.
- *Width.*—About 2 cm.
- *Shape.*—Ovate-elliptical.
- *Apex.*—Acute.
- *Base.*—Cuneate.
- *Margin.*—Usually entire, but occasionally with few broad serrations at apex.
- *Texture* (*upper and lower surfaces*).—Thick, leathery.
- *Venation pattern.*—Pinnate.
- *Venation color* (*upper and lower surfaces*).—Midrib color is 144C and secondary vein color is 147A.
- *Color of emerging foliage* (*upper surface*).—N144C.
- *Color of emerging foliage* (*lower surface*).—144C.
- *Color of mature foliage* (*upper surface*).—147A.
- *Color of mature foliage* (*lower surface*).—146B.
- *Petiole length.*—About 4 mm.
- *Petiole diameter.*—About 1 mm.
- *Fine pubescence.*—199B in color.
- *Petiole color* (*upper and lower surfaces*).—144B.

Flower description:

- *Flower type and habit.*—Apetalous flowers with a pubescent, 5-parted calyx are borne on short racemes from the leaf axils.
- *Natural flowering season.*—Late winter, approximately January to February in Watkinsville, Ga. Individual flowers are showy for approximately 1 week and are self-cleaning. The inflorescence is a raceme about 2.4 cm in length and 1.6 cm in width, consisting of 4 to 10 flowers per raceme that are 187B in color. A lateral branch may have 15 to 20 inflorescences.
- *Flower size.*—About 8 mm in diameter and about 8 mm in height.
- *Pedicels.*—About 2 mm in length.
- *Peduncles.*—About 1.2 cm in length.
- *Color.*—Pedicels and peduncles 146B in color with pubescence 166A in color.

Stamens:

- *Quantity/arrangement.*—7 to 10 per flower.
- *Filament.*—About 3 mm in length, less than 1 mm in width, and 146D in color.
- *Anthers.*—About 2 mm in length, about 1 mm in width, and 59A in color.
- *Pollen.*—Produced in moderate quantities and is 158D in color.

Pistils:

- *Position.*—Superior.
- *Size.*—About 8 mm in length and about 2.5 mm in width.
- *Color.*—146D.
- *Stigma.*—2 per pistil, about 4 mm in length, 185B in color.
- *Style.*—2 per flower, about 2 mm in length, and 146D in color.
- *Ovary.*—Two per flower, about 2 mm in diameter, about 2 mm in height, and 146D in color.

Fruit:

- *Type/appearance.*—2-valved, beaked woody capsule containing 2 seeds, one per valve.
- *Fruit size.*—The capsule is about 1.5 cm long and about 7 mm wide.
- *Mature color.*—200C.
- *Seeds.*—Oblong to elliptical in shape, about 5 mm in length, about 2 mm in width, and N200A in color.

Disease/pest resistance: Plants of the new *Distylium* grown in the nursery and garden have not been noted to be susceptible to pathogens or pests.

Weather and temperature tolerance: 'PIIDIST-I' is cold hardy in USDA Cold Hardiness Zones 6-9.

I claim:

1. A new and distinct *Distylium* plant named 'PIIDIST-I', as illustrated and described herein.

* * * * *